United States Patent
Ennenbach et al.

(10) Patent No.: US 9,428,449 B2
(45) Date of Patent: Aug. 30, 2016

(54) METHOD OF FORMING UREA BY INTEGRATION OF AN AMMONIA PRODUCTION PROCESS IN A UREA PRODUCTION PROCESS AND A SYSTEM THEREFOR

(71) Applicant: ALSTOM Technology Ltd, Baden (CH)

(72) Inventors: Frank Ennenbach, Drelelch (DE); Ulrich Koss, Baden (CH)

(73) Assignee: ALSTOM Technology Ltd, Baden (CH)

( * ) Notice: Subject to any disclaimer, the term of this patent is extended or adjusted under 35 U.S.C. 154(b) by 0 days.

(21) Appl. No.: 14/311,477

(22) Filed: Jun. 23, 2014

(65) Prior Publication Data

US 2015/0368191 A1    Dec. 24, 2015

Related U.S. Application Data

(63) Continuation of application No. PCT/IB2013/050399, filed on Jan. 16, 2013.

(51) Int. Cl.
| | |
|---|---|
| *C07F 7/08* | (2006.01) |
| *C07C 273/10* | (2006.01) |
| *C07C 273/04* | (2006.01) |
| *C01C 1/12* | (2006.01) |
| *C01C 1/04* | (2006.01) |

(52) U.S. Cl.
CPC ............... *C07C 273/10* (2013.01); *C01C 1/04* (2013.01); *C01C 1/12* (2013.01); *C07C 273/04* (2013.01)

(58) Field of Classification Search
CPC ................................ C07C 273/10; C01C 1/12
USPC ........................................................ 544/69
See application file for complete search history.

(56) References Cited

U.S. PATENT DOCUMENTS

| | | | |
|---|---|---|---|
| 4,138,434 A | 2/1979 | Laganá et al. | |
| 4,235,816 A | 11/1980 | Lagana et al. | |
| 5,523,483 A * | 6/1996 | Singh | C01B 3/025 564/68 |
| 5,985,224 A | 11/1999 | Lagana | |
| 6,093,380 A | 7/2000 | Lagana et al. | |
| 6,585,807 B2 | 7/2003 | Umino et al. | |
| 8,398,748 B2 | 3/2013 | Mak | |
| 2010/0099914 A1 | 4/2010 | Winkler | |
| 2012/0125062 A1 | 5/2012 | Blandy | |

FOREIGN PATENT DOCUMENTS

| | | | |
|---|---|---|---|
| CA | 2 331 268 A1 | 2/1999 | |
| CN | 1344711 A | 4/2002 | |
| CN | 1993317 A | 7/2007 | |
| EP | 2 070 872 A2 | 6/2009 | |
| GB | 1 359 715 | 7/1974 | |
| GB | 1359715 A * | 7/1974 | ........... C07C 273/04 |
| JP | 60146861 A | 8/1985 | |
| RU | 2196767 C2 | 1/2003 | |
| SU | 240702 A1 | 4/1969 | |
| WO | 2006/022885 A1 | 3/2006 | |
| WO | 2008/135150 A1 | 11/2008 | |

OTHER PUBLICATIONS

Decision of Grant for Russian Patent Application No. 2014133543, issued Jul. 16, 2015.

* cited by examiner

*Primary Examiner* — Profirio Nazario Gonzalez
*Assistant Examiner* — Kofi Adzamli
(74) *Attorney, Agent, or Firm* — Cynthia W. Flanigan

(57) ABSTRACT

A method of forming urea by integration of an ammonia production process with that of a urea production process, as well as a system for the method is disclosed. Also, an alternative method of forming urea by integration of a part of an ammonia production process with that of a urea production process, as well as a system for the alternative method.

20 Claims, 3 Drawing Sheets

METHOD OF FORMING UREA BY INTEGRATION OF AN AMMONIA PRODUCTION PROCESS IN A UREA PRODUCTION PROCESS AND A SYSTEM THEREFOR

CROSS-REFERENCE TO RELATED APPLICATIONS

This application claims priority to PCT/IB2013/050399 filed Jan. 16, 2013, which in turn claims priority to EP121511354.3 filed Jan. 17, 2012, both of which are hereby incorporated in their entireties.

TECHNICAL FIELD

The present invention relates to a method of forming urea by integration of an ammonia production process in a urea production process, and to a system for said method. It also relates to a method of forming urea by integration of a part of an ammonia production process in a urea production process, and to a system for said method.

BACKGROUND

In several combustion processes, and in well-known ammonia production processes, a flue gas containing, inter alia, carbon dioxide is formed. This carbon dioxide component is often separated out or captured from the flue gas in one or more absorber systems using a solvent absorber. Typically, the spent carbon dioxide solvent absorber is then regenerated in one or more regeneration columns. In carbon dioxide capture systems of this kind, there is a need to reduce system energy consumption and capital expenditure ("capex") requirements. For such solvent-based carbon dioxide capture systems, much of the energy consumption and capex are due to the need for solvent absorber regeneration, i.e., carbon dioxide desorption, in regeneration columns. Regeneration columns have high energy consumption demands due to considerable heat requirements from a reboiler or other source for carbon dioxide desorption. Solvents typically used in solvent-based carbon dioxide capture systems include amines and ammonia. For example, in an ammonia production process a solvent-based carbon dioxide capture system known as the Chilled Ammonium Process (CAP) is normally used. In CAP, ammonia is used as the solvent. Other processes including a solvent-based carbon dioxide capture system use different kinds of amines or mixtures thereof.

WO 2006/022885 discloses ultra cleaning of combustion gas including removal of carbon dioxide in an absorbing subsystem with one or more carbon dioxide absorbing stages and a subsequent regeneration subsystem.

The process for urea production is well-known and extensively disclosed in the literature. Different variants of the urea production process exist, but a common feature is that ammonia and carbon dioxide are used as reactants under elevated pressure in a urea synthesis tower or reactor for the production of urea. According thereto, the following two equilibrium reactions take place:

After the urea synthesis reaction, urea, carbamate, water and excess ammonia are transported to a distillation reactor from which a solution or slurry of, inter alia, carbamate in equlibrum with ammonia, carbon dioxide and water is recycled back to the urea synthesis reactor for further reaction.

WO 2008/135150 discloses a method for purifying flue gases from incinerators and then producing urea. In this method, ammonia and flue gas containing carbon dioxide is added to a washing device in which carbon dioxide is absorbed. A solution containing $(NH_4)_2CO_3$ and $(NH_4)_2CO_4$ is emitted from the washing unit and transported to a stripper in which $(NH_4)_2CO_4$ is separated and $(NH_4)_2CO_3$ is subjected to an energy-consuming decomposition to carbon dioxide and ammonia. This carbon dioxide and ammonia is then used in a urea production process.

GB 1 359 715 discloses an integrated process for the production of ammonia and urea including process steps comprising the absorption of carbon dioxide from a concentrated ammonia solution with a view to yielding a concentrated ammonium carbamate solution to be fed to a urea reactor, wherein the carbon dioxide source is a raw synthesis gas containing carbon dioxide and hydrogen.

Methods to reduce energy consumption and capex of solvent-based carbon dioxide capture systems have been developed, but the need for further cost reductions remain.

SUMMARY

An object of the present invention is to provide a solvent-based carbon dioxide capture system and method with reduced energy consumption demands and capital cost requirements. This object is achieved by means of a system and method of forming urea by integration of an ammonia production process in a urea production process. As a result of this integration, ammonia and carbon dioxide obtained from synthetic gas ("syngas") is formed during steam reforming or gasification in connection with the ammonia production process in an ammonia production plant. Accordingly, a first ammonia stream, a carbon dioxide stream, and a flue gas stream containing carbon dioxide are formed. The first ammonia stream is separated into a second ammonia stream for transport to an absorber, and a third ammonia stream for transport to a urea synthesis section, which may be a part of a urea synthesis reactor in a urea production plant. The carbon dioxide stream is also transported to the urea synthesis section, and the flue gas stream is transported to the absorber for carbon dioxide absorption into a mixed stream comprising the second ammonia stream and a lean solvent stream containing ammonia and a relatively low content of carbon dioxide. Following carbon dioxide absorption by the mixed stream, a rich solvent stream containing ammonia and a relatively high content of carbon dioxide is emitted from the absorber and transported to the urea synthesis section. In the urea synthesis section, carbon dioxide and ammonia are reacted for the production of urea. This production of urea produces a relatively lean solvent stream containing ammonia and a relatively low concentration of carbon dioxide for recycling from the urea production plant to the absorber.

An advantage of this method is that carbon dioxide desorption is unnecessary, since the carbon dioxide in the solvent stream is bound to ammonia, i.e., two reactants necessary for the urea production process. Thereby, by using the carbon dioxide bound ammonia in a urea production process rather than by using the carbon dioxide bound ammonia following desorption, system energy demands and capital expenses are substantially reduced.

According to one embodiment, flue gas is obtained from combustion in an ammonia production plant.

According to one embodiment of the method, combustion in an ammonia production plant is performed in a steam reformer.

According to one embodiment, a flue gas stream is cooled to a temperature of 0-25° C., preferably to a temperature of 10-20° C., before transport to an absorber.

According to one embodiment, the absorber is a CAP (Chilled Ammonia Process) absorber.

According to one embodiment, a clean gas stream is emitted from an absorber.

According to one embodiment, the concentration of ammonia in a mixed stream and in a rich solvent stream is 2-12 moles per liter solution, preferably 6-10 moles per liter solution, wherein the concentration of carbon dioxide in a lean solvent stream is 0.2-4.0 moles per liter solution, preferably 1.5-4 moles per liter solution, and wherein the concentration of carbon dioxide in the rich solvent stream is 1.0-10.0 moles per liter solution, preferably 3-6.0 moles per liter solution.

According to one embodiment, the ratio of the concentration of ammonia to the concentration of carbon dioxide in the lean solvent stream and the rich solvent stream, is 1:1 to 3:1, preferably 3:2 to 5:2.

The object of the present invention may likewise be achieved by means of an alternative method of forming urea, i.e., by integration of a part of an ammonia production process with that of a urea production process. Accordingly, in connection with an ammonia production process, a flue gas containing carbon dioxide and nitrogen from combustion is transported to a low pressure absorber and a hydrogen/carbon dioxide gas mixture from reforming steam is transported to a high pressure absorber. The high pressure absorber contains a solvent stream semi-rich with absorbed carbon dioxide. After contact with the hydrogen/carbon dioxide gas mixture, a solvent stream with ammonia and a rich or high content of carbon dioxide is emitted from the high pressure absorber and transported to a urea production plant. At the urea production plant, the transported carbon dioxide and ammonia are reacted for the production of urea. A recycle stream containing carbamate in a solution or slurry containing ammonia, carbon dioxide, and water is transported from the urea production process to a low pressure absorber. Likewise, a stream of a balance of ammonia is transported from the ammonia production unit to the low pressure absorber of the urea production plant. This alternative method is described in detail below.

According to one embodiment of the above described alternative method, a syngas stream containing hydrogen and carbon monooxide formed during the steam reforming reaction of the ammonia production process is transported to a carbon monoxide shift unit in which the carbon monoxide is converted into carbon dioxide to form the hydrogen/carbon dioxide stream.

According to one embodiment, a nitrogen containing stream is emitted from the urea production process low pressure absorber, and a hydrogen stream is emitted from the urea production process high pressure absorber. Both the nitrogen containing stream and the hydrogen stream are transported to the ammonia production unit and reacted for the production of ammonia.

According to one embodiment, an ammonia stream, optionally originating from the ammonia production unit, is added to the recycle stream used to generate a lean solvent stream containing ammonia and a relatively low content of carbon dioxide.

According to one embodiment, a slip stream diverted from the relatively rich solvent stream is transported to the low pressure absorber.

According to one embodiment, a partial stream of the relatively lean solvent stream is added to the high pressure absorber or to the semi rich solvent stream.

According to one embodiment, a partial stream of the semi rich solvent stream is transported to the urea production plant.

According to one embodiment, the pressure in the low pressure absorber is 0.08-0.15 MPa, preferably 0.095-0.11 MPa, and the pressure in the high pressure absorber is 0.3-4.0 MPa, preferably 0.095-0.11 MPa.

According to one embodiment, the concentration of ammonia in the relatively lean solvent stream, in the semi rich solvent stream and in the relatively rich solvent stream is 2-12, preferably 6-9, moles per liter solution.

According to one embodiment, the concentration of carbon dioxide in the relatively lean solvent stream is 0.2-4.0, preferably 1.5-4.0, moles per liter solution, the concentration of carbon dioxide in the semi rich solvent stream is 1.0-5.5, preferably 2.5-4.5, moles per liter of solution, and the concentration of carbon dioxide in the relatively rich solvent stream is 1.0-10.0, preferably 3.0-6.0, moles per liter solution.

According to one embodiment, the ratio between the concentration of ammonia and the concentration of carbon dioxide in the lean, semi rich, and rich solvent streams, respectively, is 1:3, preferably 1.5:2.5.

A further object of the present invention is to provide systems in which the integrated method and the alternative integrated method are performed.

This further object is achieved by a system for the integrated method of forming urea by integration of an ammonia production process with that of a urea production process, wherein said system comprises an ammonia production plant, an absorber, and a urea synthesis section in a urea production plant. Said system includes a conduit for a first ammonia stream from the ammonia production plant separated into a conduit for a second ammonia stream fluidly connected to the absorber, or to a conduit for a lean solvent stream thus forming a mixed stream, and into a conduit for a third ammonia stream fluidly connected to the urea synthesis section. Likewise, a conduit for a flue gas stream containing carbon dioxide is fluidly connected between the ammonia production plant, or another flue gas source, and the absorber. A conduit for a carbon dioxide stream is fluidly connected between the ammonia production plant and the urea synthesis section. A conduit for a rich solvent stream is fluidly connected between the absorber and the urea synthesis section, and a conduit for a lean solvent stream is arranged between the urea production plant and the absorber.

According to one embodiment, this system comprises a conduit for a clean gas stream fluidly connected to the absorber.

This further object is achieved through an alternative integrated method with a system for forming urea by integration of a part of an ammonia production process with that of a urea production process. Such a system comprises a steam reformer or a gasification reactor of an ammonia production plant, a low pressure absorber, a high pressure absorber, and a urea production plant, wherein a conduit for a flue gas stream is fluidly connected between the steam reformer, or the gasification reactor, and the low pressure absorber. A conduit for a hydrogen/carbon dioxide stream is arranged between the steam reformer, the gasification reactor, or another flue gas source, and the high pressure absorber. A conduit for a semi rich solvent stream is fluidly connected between the low pressure absorber and the high pressure absorber. A conduit for a rich solvent stream is fluidly connected between the high pressure absorber and the urea production plant, and a conduit for a lean solvent stream is fluidly connected between the urea production plant and the low pressure absorber.

According to one embodiment of the alternative integrated method, the system comprises an ammonia production unit, a conduit for a hydrogen stream fluidly connected between the high pressure absorber and the ammonia production unit, and a conduit for a nitrogen containing stream fluidly connected between the low pressure absorber and the ammonia production unit. The system also comprises a conduit for a stream of the balance of ammonia fluidly connected between the ammonia production unit and the urea production plant.

According to one embodiment, the system comprises a carbon monoxide shift unit for the conversion of carbon monooxide into carbon dioxide, wherein a conduit for a syngas stream containing hydrogen and carbon monoxide is fluidly connected between the steam reformer, or the gasification reactor, and the carbon monoxide shift unit. Likewise, the conduit for the hydrogen/carbon dioxide stream is fluidly connected between the carbon monooxide shift unit and the high pressure absorber.

According to one embodiment, the system comprises a conduit for a partial stream of the semi rich solvent stream fluidly connected between the conduit for the semi rich solvent stream and the conduit for the rich solvent stream.

According to one embodiment, the system comprises a conduit for a recycle stream containing carbamate in a solution or in a slurry also containing ammonia, carbon dioxide and water, fluidly connected between the urea production plant and the conduit for the lean solvent stream. Likewise, a conduit for an ammonia stream is fluidly connected to the conduit for the recycle stream.

According to one embodiment, the system comprises a conduit for a partial stream of the lean solvent stream fluidly connected between the conduit for the lean solvent stream and the conduit for the semi rich solvent stream or the high pressure absorber.

BRIEF DESCRIPTION OF THE DRAWINGS

Referring now to the figures, which are exemplary embodiments, and wherein the like elements are numbered alike.

DETAILED DESCRIPTION

Figure 1:
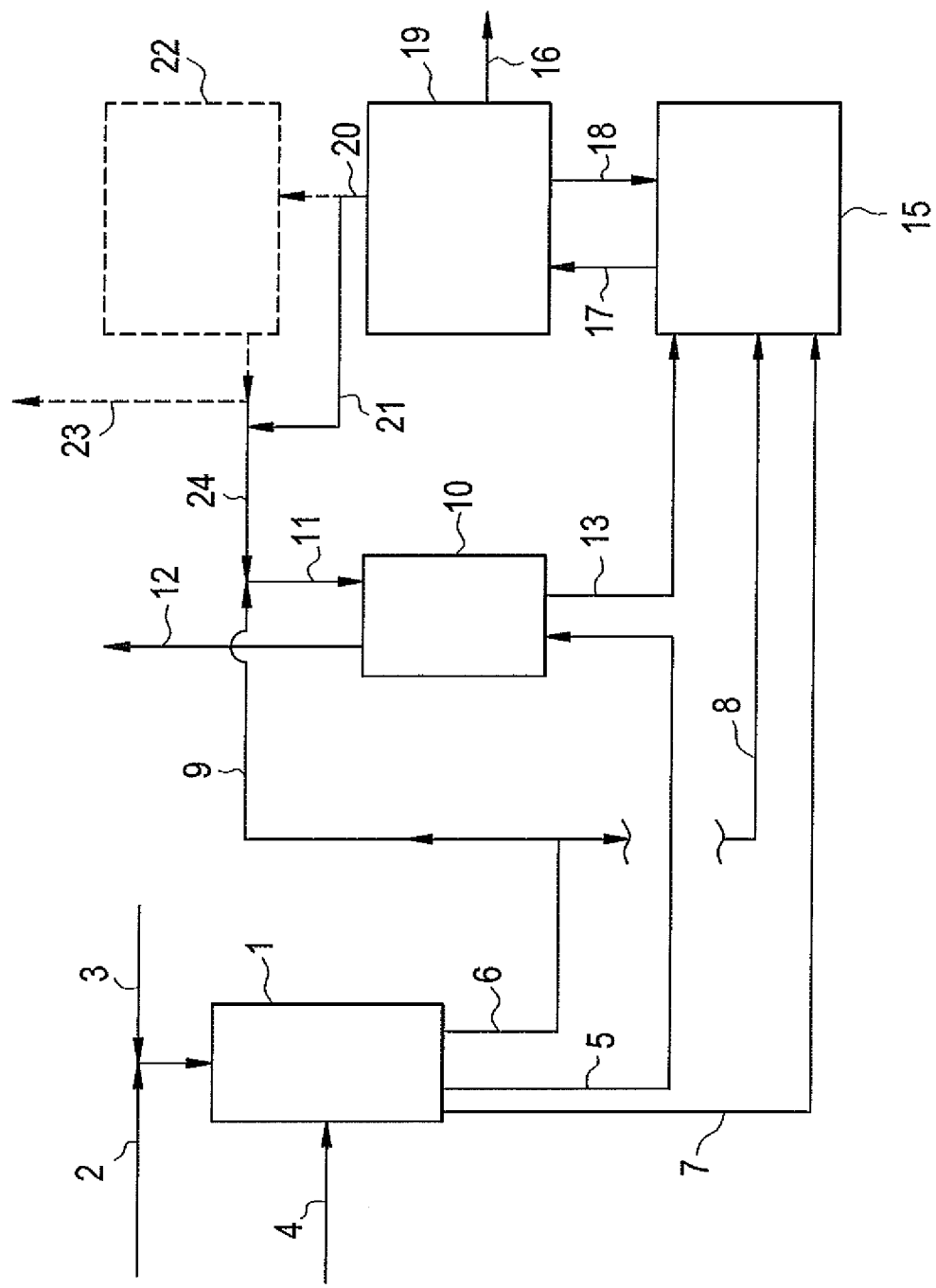
FIG. 1 is a schematic view of a system used for the method of forming urea by integration of an ammonia production process with a urea production process.

Carbon dioxide used as a reactant for a urea production process according to the present integrated method may originate from any combustion plant or apparatus, e.g., a conventional reformer. In one embodiment, the carbon dioxide originates from a steam reformer combustion apparatus part of an ammonia production process.

Syngas, also called synthetic gas or synthesis gas, is produced when hydrocarbons react with water in a reactor apparatus, e.g., a steam reformer. Syngas is a gas mixture containing varying amounts of carbon monoxide and hydrogen. A steam reformer used to produce syngas is a tubular reactor fired from the outside to providing sufficient reaction energy for a reforming reaction. For this purpose, a fuel is subjected to combustion in the fire box on the outer side of the steam reformer tubes. Inside the tubes of a steam reformer, the steam reforming reaction takes place in the presence of a catalyst to produce syngas. Carbon monoxide in the syngas is subjected to a carbon monoxide shift reaction with water to produce carbon dioxide. After such production, the carbon dioxide is then separated from the hydrogen. The separated hydrogen is then reacted with nitrogen in the air to produce ammonia. In addition to the use of hydrogen as a reactant for ammonia production and the use of carbon dioxide produced from the carbon monoxide shift reaction, useful flue gases are also formed from the combustion of the fuel for the steam reformer. These flue gases contain nitrogen, carbon dioxide and other contaminants, e.g., NOx. Normally, the carbon dioxide present in the flue gas in an ammonia production process can be absorbed in a CAP (Chilled Ammonia Process) absorber operating at atmospheric pressure and a low temperature. Before entering the CAP absorber, the flue gas is cooled to enhance absorption of the carbon dioxide by a carbon dioxide-lean ammoniated solution present in the absorber. After the carbon dioxide absorption step, the once carbon dioxide-lean ammoniated solution is a carbon dioxide rich solution that requires regeneration in a subsequent regeneration step. This process is disclosed more in detail in WO 2006/022885.

Another method for syngas production is gasification of a carbon or hydrocarbon with oxygen in a gasification reactor. Here, the reaction energy is provided within the gasification reactor itself. Syngas so produced can be treated as described above to separate the hydrogen from the carbon dioxide. However, in accordance with the present process there is a need for another flue gas source to produce additional carbon dioxide. Under such circumstances, the same integration scheme as applied for steam reformers can be similarly applied hereto.

Thus, syngas used in the present method is either formed in a steam reformation reaction or in a gasification reaction. In the steam reformation reaction, flue gas is produced by combustion during steam reforming. In the gasification reaction, the flue gas may originate from any source. The language "ammonia production process" and "ammonia production plant" used herein is intended to cover both of these reactions.

The integrated method and system will now be disclosed more in detail with reference to FIG. 1, which illustrates the embodiment when both the syngas and the flue gas are formed during steam reformation. According to FIG. 1, an ammonia production plant 1 comprising a steam reformer 1a (not shown) for combustion is provided with a feedstock 2, e.g., natural gas, oil or hydrocarbons, and steam 3. The steam reformer 1a is fired with a fuel 4, e.g., natural gas. During the reaction between hydrocarbons and steam in the steam reformer 1a, syngas is produced. A flue gas is also produced from firing of the steam reformer 1a. A flue gas stream 5 containing carbon dioxide and other contaminants is transported, optionally via one or more conventional purification steps, to a CAP absorber 10, in which carbon dioxide is absorbed. Further, a first ammonia stream 6 containing ammonia from the reaction between hydrogen in the syngas and nitrogen from the air in the ammonia production plant 1 is separated into a second ammonia stream 9 and a third ammonia stream 8. Ammonia stream 9 is added to a lean solvent stream 24 before reaching CAP absorber 10. The lean solvent stream 24 of recycled carbamate in a solution or slurry, also containing water, ammonia, and a low content of carbon dioxide, from a urea production process is added to the CAP absorber 10 as a mixed stream 11. Mixed stream 11 is a mixture of the second ammonia stream 9 and the lean solvent stream 24. In the CAP absorber 10, carbon dioxide in the flue gas stream 5 is absorbed in the solution of the mixed stream 11 to produce a clean gas stream 12. Clean gas stream 12 of treated flue gas having a low carbon dioxide content is emitted from the CAP absorber 10. A rich solvent stream 13 containing ammonia, water, and a high content of carbon dioxide is emitted from CAP absorber 10 and transported under a high pressure, suitable for any urea synthesis reaction, to a urea synthesis section 15 in a urea production plant 15a (not shown). In the urea synthesis section 15, carbon dioxide and ammonia are reacted to produce urea. A mixture of urea produced, carbamate, excess ammonia and water is then transported in a stream 17 to a stripper section 19 from which urea is separated in several steps in a urea stream 16. Ammonia and carbon dioxide from stripper section 19 are emitted in a stream 20 in the form of a carbamate solution containing ammonia, carbon dioxide and water. Stream 20 or a part of stream 20 is then transported as such in a stream 21, and as such in lean solvent stream 24, to the absorber 10. The balance in stripper section 19 is recyled back as a stream 18 to the urea synthesis section 15 or to any other suitable place in urea production. Optionally, the stream 20 is subjected to waste water treatment in a waste water treatment unit 22, wherein water is separated from stream 20 to produce a water stream 23. Instead of recycling the stream 20 back to the urea synthesis section 15, as in a conventional urea production process, all or a part of stream 20 is transported to the absorber 10 for use in the ammonia production process in the form of the lean solvent stream 24. The third ammonia stream 8 originating from first ammonia stream 6 is transported directly to the urea synthesis section 15 in the urea production plant 15a.

Further, a carbon dioxide stream 7 containing carbon dioxide originating and separated from the syngas produced in the ammonia production plant is transported directly to the urea synthesis section 15. The production of syngas may be designed for obtaining a sufficient amount of carbon dioxide for urea production, which will lead to some excess of ammonia. An additional carbon dioxide source would be any flue gas. If the carbon dioxide is taken from the flue gas, either the syngas production can be reduced (adjusted according to the desired level of ammonia production), or alternatively, any excess ammonia can be used in the urea production process to increase urea production. Such is accomplished by feeding additional carbon dioxide from the flue gas source as noted previously. Further, the lean solvent stream 24 of the recycled carbamate may be taken from any suitable place in the urea production plant 15a. It should be noted that each of the various streams described herein are transported in fluidly connected conduits, suitable for such purpose.

As disclosed above, first ammonia stream 6 and carbon dioxide stream 7 could alternatively be obtained from a syngas produced in a gasification reactor (not shown in FIG. 1). Likewise, flue gas stream 5 containing carbon dioxide could be provided from any other source (not shown in FIG. 1, such as a boiler, e.g. a power boiler or any boiler supplying heat to a urea production plant).

Any other carbon dioxide capture technologies not using an ammoniated solvent cannot be integrated into the urea process as described herein, since the carbon dioxide absorbent solvent would comprise a chemical foreign to the urea production process, which would disturb urea production or even make it impossible. Further, the flue gas stream 5 may be subjected to any conventional cleaning or separation processes not shown in FIG. 1 before it is transported to the CAP absorber 10. The carbon dioxide source for the urea production process may also originate from, e.g., any fossil fuel fired boiler or process heater in the urea production plant 15a or elsewhere.

Thus, the need for a carbon dioxide desorption/solvent regeneration process as used in the conventional carbon dioxide capture process is eliminated in the present integrated method, thereby reducing energy and equipment costs.

The language "lean solvent" and "rich solvent" as used herein means a concentration of ammonia in the lean solvent stream 24 and in the rich solvent stream 13 of 2-12, preferably 6-10, moles per liter solution, a concentration of carbon dioxide in the lean solvent stream 24 of 0.2-4.0, preferably 1.5-4, moles per liter solution and a concentration of carbon dioxide in the rich solvent stream 13 of 1.0-10.0, preferably 3.0-6.0, moles per liter solution. The ratio of the concentration of ammonia to the concentration of carbon dioxide in the rich solvent stream 13 is 1:1 to 3:1, preferably 3:2 to 5:2, in order to satisfy the stochiometrics of the urea reaction. If further ammonia is added via the second ammonia stream 9, the above-mentioned ammonia concentrations in the mixed stream 11 and the rich solvent stream 13 will be changed.

Figure 2:
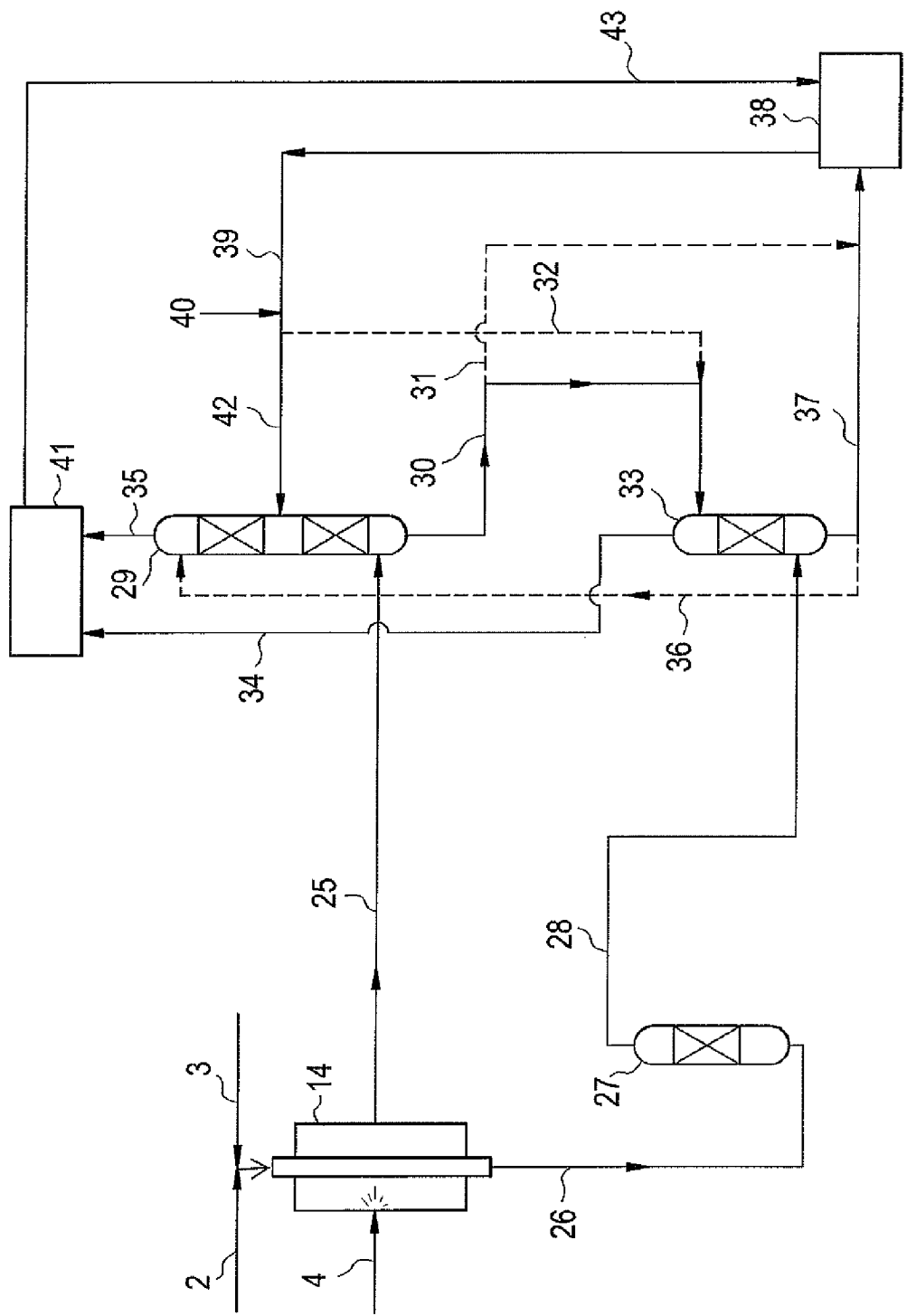
FIG. 2 is a schematic view of a system for the alternative integrated method of forming urea by integration of a part of an ammonia production process with a urea production process.

In the embodiment of the alternative integrated method and system illustrated in FIG. 2, carbon dioxide produced in the ammonia production process is not per se integrated with the urea production process. Instead, a rich solvent stream from the absorption of the gas mixture of hydrogen and carbon dioxide (formed via a carbon monooxide shift reaction), originating from syngas produced in a steam reformer 14 or a gasification reactor during the ammonia production process, is used for the integration.

More precisely, hydrogen is typically produced during syngas production by steam reforming or gasification. Typically, physical absorption or adsorption processes are applied to separate the carbon dioxide from the hydrogen in the gas mixture of hydrogen and carbon dioxide. This occurs at elevated pressures, often much higher than those used during carbon dioxide absorption from flue gas in a high pressure absorber. After separation of carbon dioxide, the hydrogen is reacted with nitrogen in the air to form ammonia.

In the present alternative integrated method, both the flue gas stream and the stream of the gas mixture of hydrogen and carbon dioxide, originating from the syngas stream, are subjected to carbon dioxide absorption. If the chilled ammonia process (CAP) is applied to absorb carbon dioxide from the stream of the gas mixture of carbon dioxide and hydrogen, it is also possible to use the lean solvent stream containing carbamate from the urea process, if necessary enriched with additional ammonia. Then a low pressure absorber for the flue gas and a high pressure absorber for the gas mixture of carbon dioxide and hydrogen are needed. Said lean solvent may be used either in parallel to the low pressure absorber for flue gas or in sequence, using a semi rich solvent for the absorption of carbon dioxide in the high pressure absorber. Both the semi rich solvent and the rich solvent formed after high pressure absorption is fed back to the urea production plant 15a, preferably direct to the urea synthesis section 15 therein.

The advantages of this alternative integrated method are as follows. First, a combination of the two absorption processes (of carbon dioxide from flue gas and from syngas, respectively) using the same kind of solvent and same kind of principle (wet absorption) is obtained. Second, any need for desorption of carbon dioxide from the rich solvent is eliminated, since this rich solvent is used for the urea reaction. The rich solvent already contains ammonia and carbon dioxide as reactants for the urea process significantly reducing associated energy and equipment costs. Third, no "foreign" chemical is added, such as an amine, as used in some carbon capture processes.

Further, potentially the carbon dioxide lean and nitrogen rich flue gas stream following absorption can be used as feedstock for ammonia synthesis to replace at least a part of the air used for ammonia synthesis. Such could allow for increased ammonia production, since less oxygen containing air is then fed to the synthesis. Any smaller amounts of ammonia slippage into either the hydrogen stream or the nitrogen rich stream from the absorbers should not poison the ammonia synthesis reaction. As an option, a slip stream from the rich solution stream may be transported to the low pressure absorber to minimize ammonia slippage into the nitrogen rich stream.

This embodiment of the alternative integrated method and system for the formation of urea by integration of a part of an ammonia production process with the urea production process is schematically illustrated in FIG. 2 and will be disclosed in detail below with reference to FIG. 2. Although a steam reformer unit 14 is illustrated in FIG. 2, such could, in analogy with the system illustrated in FIG. 1, as an alternative be a gasification reactor in which syngas is formed. In that case, the flue gas used in the alternative integrated method is provided from any other source (not shown in FIG. 2), such as a boiler, e.g. a power boiler or any boiler supplying heat to a urea production plant. Referring to FIG. 2 a steam reformer 14 is provided with a feedstock 2, e.g., natural gas, oil, or hydrocarbons, and with steam 3. The steam reformer 14 is fired with a fuel 4, e.g., natural gas. During the reaction between carbohydrates and steam in the steam reformer 14 a syngas containing hydrogen and carbon monooxide is produced. A syngas stream 26 is transported to a carbon monooxide shift unit 27, in which the carbon monooxide is subjected to a shift into carbon dioxide. The hydrogen/carbon dioxide stream 28 so obtained is transported directly to a high pressure absorber 33 having a pressure of 0.3-4 MPa, preferably 1-2.5 MPa. Further, a flue gas containing nitrogen, carbon dioxide, and other contaminants is emitted from the steam reformer 14, and transported as flue gas stream 25 to a low pressure absorber 29 having a pressure of 0.08-0.15 MPa, preferably 0.095-0.11 MPa.

In the high pressure absorber 33 carbon dioxide is absorbed and is then emitted therefrom in a rich solvent stream 37 containing carbon dioxide in a high concentration, water, and ammonia. This rich solvent stream 37 is then transported under a high pressure as a reactant to the urea synthesis reactor 38a (not shown) in a urea production plant 38. A hydrogen stream 34 is emitted from the high pressure absorber 33 for use as a reactant in an ammonia production unit 41. Optionally, a slip stream 36 of rich solvent stream 37 is transported to the top of the low pressure absorber 29, where it is used to catch excess ammonia from the upcoming treated flue gas stream 25 as necessary, before the cleaned flue gas, i.e., nitrogen containing stream 35, is transported to the ammonia production unit 41 for usage.

In the low pressure absorber 29 carbon dioxide contained in the flue gas stream 25 is absorbed by means of lean solvent stream 42. Such leaves low pressure absorber 29 as a semi rich solvent stream 30 containing absorbed carbon dioxide in a medium concentration, water, and ammonia. This semi rich solvent stream 30 is then transported to high pressure absorber 33. Optionally, a partial stream 31 of the semi rich solvent stream 30 is transported to the urea production plant 38. Before entering the low pressure absorber 29, flue gas stream 25 may be subjected to one or more conventional purification steps, and is also cooled to a temperature of between 0 and 25° C., preferably to a temperature between 10 and 20° C. Cleaned flue gas containing nitrogen at a high percentage, which is emitted from the low pressure absorber 29, can be transported as the nitrogen containing stream 35 to the ammonia production unit 41. Thus, the hydrogen in the hydrogen stream 34 and the nitrogen in the nitrogen containing stream 35 are transported as reactants to the ammonia production unit 41 in which the reaction between hydrogen and nitrogen takes place to produce ammonia. A recycle stream 39 containing a mixture of ammonium carbamate, ammonium carbonate and ammonium bicarbonate, either in solution or in a slurry, also containing unreacted ammonia, carbon dioxide, carbonic acid and water originating from the urea production plant 38, is optionally provided with additional ammonia via an ammonia stream 40 from the ammonia production unit 41 forming a lean solvent stream 42 in the form of a ammonia solution containing carbon dioxide in a low concentration, ammonia, ammonium carbamate, ammonium carbonate, ammonium bicarbonate and water, wherein this lean solvent stream 42 is transported to the low pressure absorber 29. Optionally, a partial stream 32 of the lean solution stream 42 may be transported directly to the high pressure absorber 33 or to the semi rich solvent stream 30. The balance of ammonia from the ammonia production unit 41 is transported in partial stream 43 to the urea production plant 38.

The concentration of ammonia in the lean solvent stream 42, in the semi rich solvent stream 30 and in the rich solvent stream 37 is 2-12, preferably 6-10, moles per liter of solution. The concentration of carbon dioxide in the lean solvent stream 42 is 0.2-4.0, preferably 1.5-4, moles per liter solution. The concentration of carbon dioxide in the semi rich solvent stream 30 is 1.0-5.5, preferably 2.5-4.5, moles per liter solution. The concentration of carbon dioxide in the rich solvent stream 13 is 1.0-10.0, preferably 3.0-6.0, moles per liter solution. The ratio between the concentration of ammonia and the concentration of carbon dioxide in stream 37 is preferably 1:1.5 to 1:2.5 in order to satisfy the stochiometrics of the urea reaction.

Figure 3:
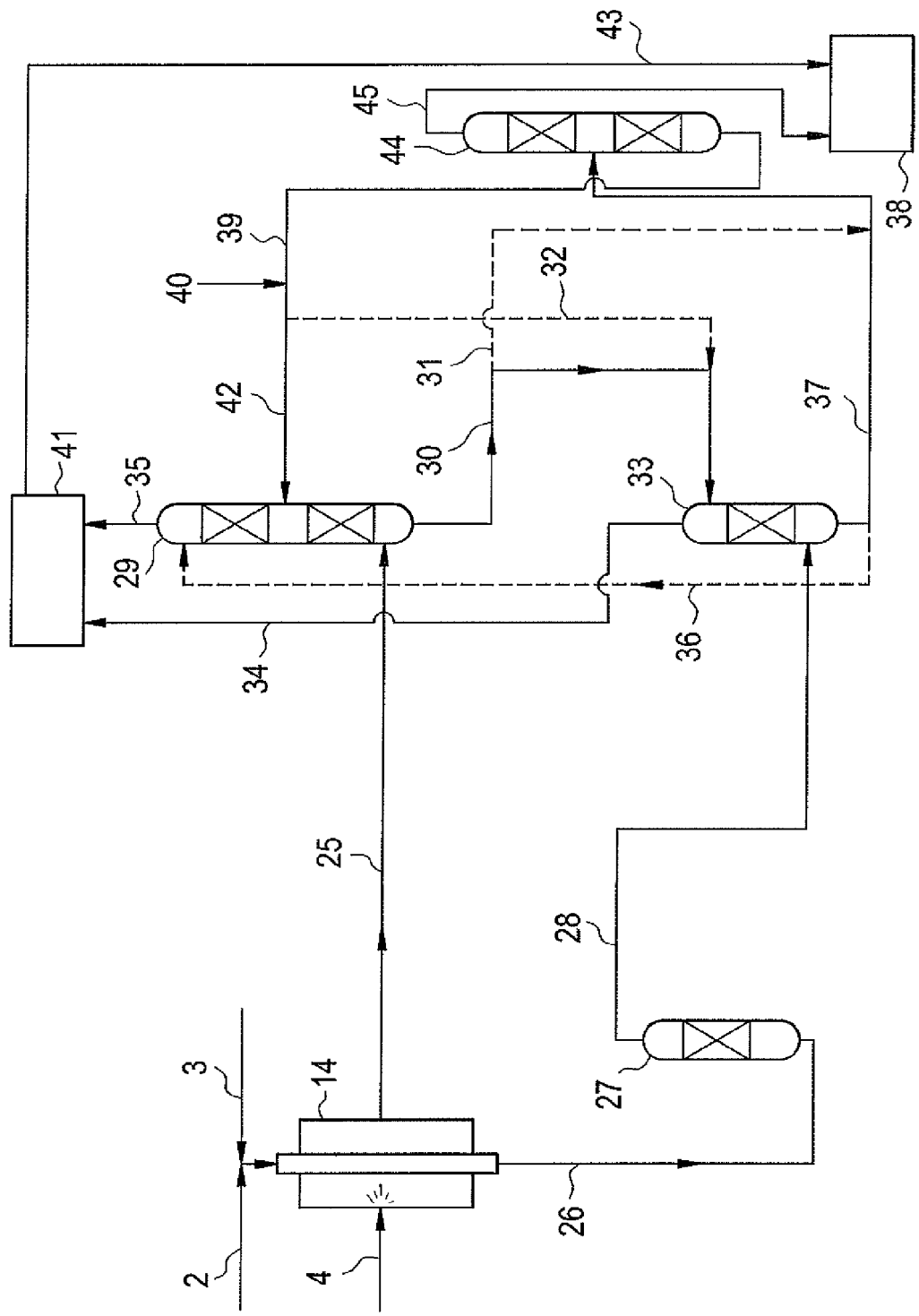
FIG. 3 is a schematic view of a system based on the system shown in FIG. 2, but also comprises a regenerator located between the high pressure absorber and the urea production plant.

FIG. 3 shows a further embodiment of the system shown in FIG. 2, wherein a regenerator 44 is located between the high pressure absorber 33 and the urea production plant 38. More precisely, the rich solvent stream 37, optionally mixed with the partial stream 31 of the semi rich solvent stream 30, is separated in the regenerator 44 to a pure $CO_2$ stream 45 and to the lean solvent recycle stream 39. The pure $CO_2$ stream 45 is fed in a conduit to the urea production plant 38, and the recycle stream 39 is fed in a conduit to the pressure absorber 29.

To summarize, the present invention relates to a method of forming urea by integration of an ammonia production process in a urea production process, and to a system for said method. It also refers to an alternative method of forming urea by integration of a part of an ammonia production process in a urea production process, and to a system for said alternative method.

While the invention has been described with reference to a number of preferred embodiments, it will be understood by those skilled in the art that various changes may be made and equivalents may be substituted for elements thereof without departing from the scope of the present invention. In addition, many modifications may be made to adapt a particular situation or material to the teachings of the invention without departing from the essential scope thereof. Therefore, it is intended that the invention not be limited to the particular embodiments disclosed as the best mode contemplated for carrying out this invention, but that the invention will include all embodiments falling within the scope of the appended claims.

The invention claimed is:

1. A method of forming urea by integration of an ammonia production process in a urea production process comprising:
obtaining ammonia and carbon dioxide and a flue gas for a first ammonia stream, a carbon dioxide stream, and a flue gas stream containing carbon dioxide;
separating the first ammonia stream into a second ammonia stream and a third ammonia stream, wherein the second ammonia stream is transported to an absorber and the third ammonia stream is transported to a urea synthesis section of the urea production process for the production of urea;
transporting the carbon dioxide stream to the urea synthesis section;
transporting the flue gas stream to the absorber;
combining the second ammonia stream and a lean solvent stream provided from the urea production process to form a mixed stream;
contacting the mixed stream with the flue gas stream in the absorber to absorb carbon dioxide from the flue gas stream to form a rich solvent stream and a treated gas stream;
transporting the rich solvent stream emitted from the absorber to the urea synthesis section;
contacting the carbon dioxide stream, the third ammonia stream and the rich solvent stream in the urea synthesis section to form urea and the lean solvent stream; and
transporting the lean solvent stream from the urea production process to the absorber.

2. The method according to claim 1, wherein the flue gas stream is obtained during combustion in an ammonia production plant.

3. The method according to claim 2, wherein the combustion in the ammonia production plant is performed in a steam reformer.

4. The method according to claim 1, wherein the flue gas stream is cooled to a temperature of 0-25 deg C. before entering the absorber.

5. The method according to claim 1, wherein the absorber is a Chilled Ammonia Process (CAP) absorber.

6. The method according to claim 1, wherein at least a portion of the treated gas stream leaving the absorber is transported to the ammonia production process.

7. The method according to claim 1, wherein the concentration of ammonia in the mixed stream and in the rich solvent stream is 2-12 moles per liter solution, the concentration of carbon dioxide in the lean solvent stream is 0.2-4.0 moles per liter solution, and the concentration of carbon dioxide in the rich solvent stream is 1.0-10.0 moles per liter solution.

8. The method according to claim 1, wherein the ratio between the concentration of ammonia and the concentration of carbon dioxide in the rich solvent stream is 1:1 to 3:1, preferably 3:2 to 5:2.

9. A method of forming urea by integration of a part of an ammonia production process in a urea production process, comprising:
obtaining a hydrogen/carbon dioxide stream from the ammonia production process, and a flue gas stream containing carbon dioxide and nitrogen;
transporting the flue gas stream to a low pressure absorber;
contacting the flue gas stream with a lean solvent stream provided from the urea production process in the low pressure absorber to produce a semi-rich solvent stream and a cleaned gas stream containing nitrogen;
transporting the hydrogen/carbon dioxide stream to a high pressure absorber;
transporting the semi-rich solvent stream from the low pressure absorber to the high pressure absorber;
contacting the hydrogen/carbon dioxide stream with the semi-rich solvent stream in the high pressure absorber to form a rich solvent stream and a hydrogen stream;
transporting the rich solvent stream from the high pressure absorber to the urea production process to form urea and the lean solvent stream comprising a solution of carbamate, ammonia, carbon dioxide and water;
transporting the lean solvent stream to the low pressure absorber, and
transporting a stream from an ammonia production unit to the urea production process.

10. The method according to claim 9, wherein the flue gas stream is obtained during combustion in a steam reformer in the ammonia production process.

11. The method according to claim 9, wherein a syngas stream containing hydrogen and carbon monoxide, and formed during a steam reforming reaction of the ammonia production process, is transported to a carbon monoxide shift unit in which the carbon monoxide is converted into carbon dioxide to form the hydrogen/carbon dioxide stream.

12. The method according to claim 9, further comprising transporting the cleaned gas stream containing nitrogen and the hydrogen stream to the ammonia production process and reacting both for the production of ammonia.

13. The method according to claim 9, wherein an ammonia stream is added to the lean solvent stream before entering the low pressure absorber.

14. The method according to claim 9, wherein at least a portion of the rich solvent stream emitted from the high pressure absorber is transported to the low pressure absorber.

15. The method according to claim 9, wherein at least a portion of the lean solvent stream is added to the high pressure absorber.

16. The method according to claim 9, wherein a partial stream of the semi rich solvent stream exiting the low pressure absorber is transported to the urea production plant.

17. The method according to claim 9, wherein the pressure in the low pressure absorber is 0.08-0.15 MPa, and the pressure in the high pressure absorber is 0.3-4.0 MPa.

18. The method according to claim 17, wherein the pressure in the low pressure absorber is 0.095-0.11 MPa, and the pressure in the high pressure absorber is 1-2.5 MPa.

19. The method according to claim 9, wherein the concentration of carbon dioxide in the lean solvent stream is 0.2-4.0 moles per liter solution, the concentration of carbon dioxide in the semi rich solvent stream is 1.0-5.5 moles per liter of solution, and the concentration of carbon dioxide in the rich solvent stream is 1.0-10.0 moles per liter solution.

20. The method according to claim 9, wherein the ratio between the concentration of ammonia and the concentration of carbon dioxide in the rich solvent stream is 1:1 to 3:1, preferably 3:2 to 5:2.

\* \* \* \* \*